United States Patent [19]
Nguyen et al.

[11] Patent Number: 5,750,446
[45] Date of Patent: May 12, 1998

[54] ABSORBENT BODY

[75] Inventors: Hien Nguyen, East Windsor, N.J.; Nicolas Martens, Wuppertal, Germany; Glenn Garbolino, Edison, N.J.

[73] Assignee: McNeil-PPC, Inc., Skillman, N.J.

[21] Appl. No.: 577,570

[22] Filed: Dec. 22, 1995

[51] Int. Cl.$^6$ .............. A61F 13/22; A61L 15/16; D04H 1/44

[52] U.S. Cl. .............. 442/337; 19/145.5; 19/296; 156/62.2; 264/122; 428/74; 604/375; 604/379; 604/380

[58] Field of Search .............. 442/337; 264/122; 156/62.2; 19/145.5, 296; 604/375, 379, 380

[56] References Cited

U.S. PATENT DOCUMENTS 4,129,679  12/1978  Woodings ............... 428/398
5,458,963  10/1995  Meirowitz et al. ............... 442/337

FOREIGN PATENT DOCUMENTS

| 0 301 874A | 2/1989 | European Pat. Off. . |
| 301874 | 2/1989 | European Pat. Off. . |
| 0 716 170A | 6/1996 | European Pat. Off. . |
| 947183 | 1/1964 | United Kingdom . |
| 2 085 304 | 4/1982 | United Kingdom . |

*Primary Examiner*—James C. Cannon
*Attorney, Agent, or Firm*—Joel A. Rothfus

[57] ABSTRACT

An absorbent body formed of an absorbent web having a blend of multi-limbed regenerated cellulosic fibers and non-limbed cellulosic fibers has surprisingly improved specific absorption capacity. This absorbent body may be in the form of sanitary napkins, tampons, diapers, and adult incontinence devices.

14 Claims, 2 Drawing Sheets

ABSORBENT BODY

FIELD OF THE INVENTION

The present invention relates to an absorbent body having improved absorption characteristics. The body has a mixture of a staple fibers having a multi-limbed cross-section having at least three limbs and non-limbed fibers. The combination of fibers provides improved specific absorption capacity over an absorbent body formed of either the multi-limbed fibers alone or the non-limbed fibers alone.

BACKGROUND OF THE INVENTION

Absorbent bodies are limited in their absorbent or absorption capacity. Thus, they cannot continue to absorb fluids once their absorption capacity is reached. Thus, researchers continue to search for improved absorption characteristics in absorbent bodies.

One solution has been to employ superabsorbent materials in absorbent bodies. These materials absorb liquids and swell into a gel-like substance. While these materials have been accepted for some uses in absorbent articles, they have yet to achieve acceptance for all uses.

Developments in cellulosic fiber technology have helped increase the absorption capacities of absorbent bodies based on these fibers. For example, Courtaulds PLC, EP 0 301 874 B1 discloses that regenerated cellulosic fibers which have a multi-limbed cross-section also have increased absorbency. While this technology is a welcomed improvement, researchers continue to look for even more improvements in absorption capacity.

Therefore, what is needed is a fibrous absorbent body having improved absorption characteristics.

SUMMARY OF THE INVENTION

We have found that improvements to the absorption capacity of absorbent bodies can be achieved by adding non-limbed cellulosic fibers to multi-limbed regenerated cellulosic fibers having at least three limbs to form an absorbent body. These non-limbed cellulosic fibers generally provide a lower specific absorption capacity than the multi-limbed fibers. As used here in the specification and claims, the term "specific absorption capacity" denotes the mass of fluid absorbed by a fibrous absorbent body per unit of mass of the absorbent body in a dry state. As used here in the specification and claims, the term "cellulosic fiber" means that the fiber contains or is derived from cellulose, e.g., natural fibers containing cellulose, such as cotton, and man-made fibers derived from cellulose, such as cellulose acetate.

What is unexpected is that the addition of the less absorbent, non-limbed fibers actually increases the specific absorption capacity of absorbent bodies comprising the multi-limbed fibers. Thus, the fibers are added in an amount effective to increase the specific absorption capacity of the absorbent body. Preferably, the non-limbed fibers are present in an amount to increase the specific absorption capacity of the absorbent body to about 105% of the specific absorption capacity of a similar absorbent body of 100 wt-% multi-limbed fibers.

DETAILED DESCRIPTION OF THE INVENTION

Figure 1:
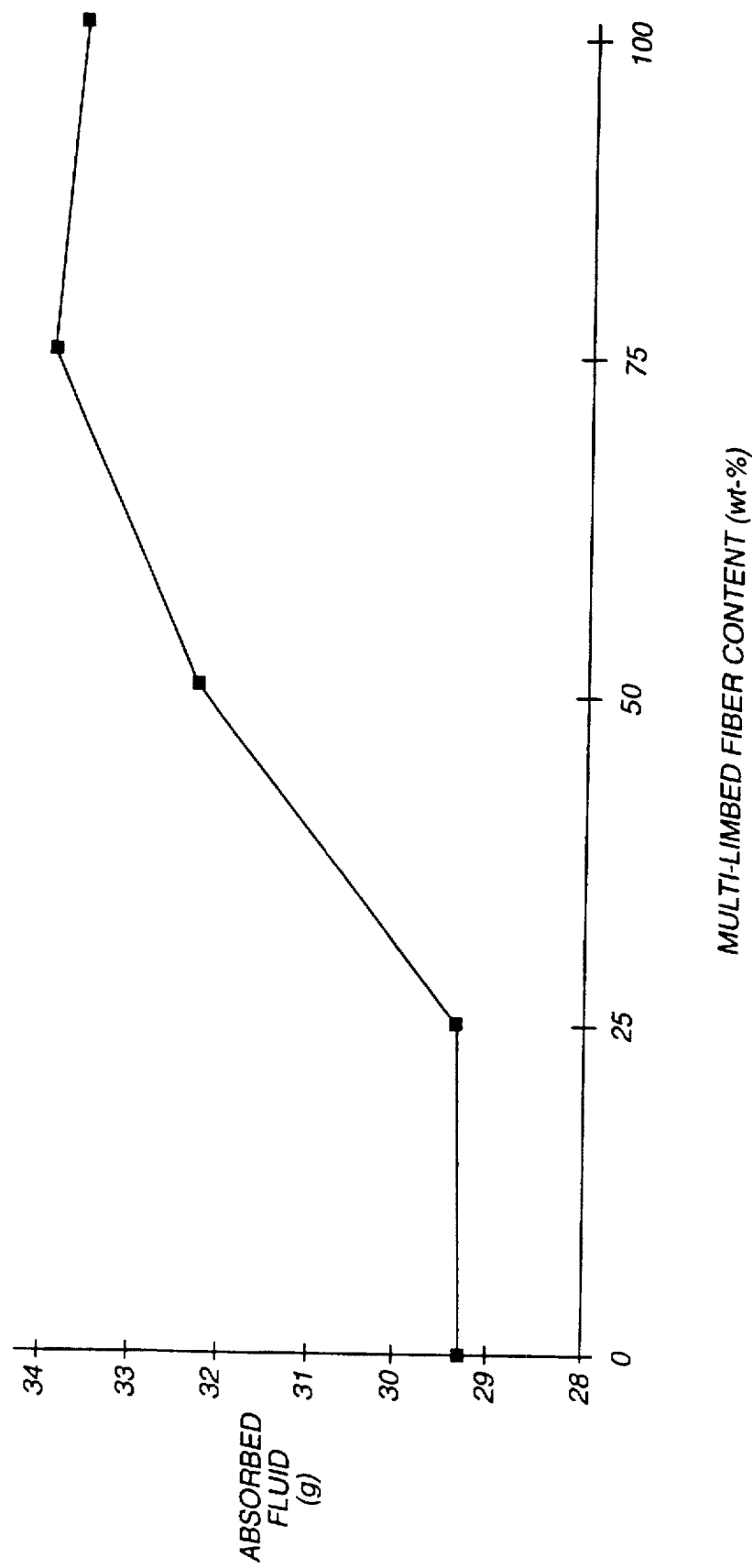
FIG. 1 illustrates a graphical representation of the data of Example 1.

The present invention takes advantage of the increased absorbency of multi-limbed, regenerated cellulosic fibers and improves this absorbency by adding an effective, specific absorption capacity-improving amount of non-limbed cellulosic fibers. Multi-limbed, regenerated cellulosic fibers have been commercially available for a number of years. These fibers are known to possess increased specific absorbency over non-limbed fibers. One commercial example of these fibers are the Galaxy® viscose rayon fibers available from Courtaulds PLC, London, England. These fibers are described in detail in Courtaulds PLC, EP0 301 874 B1, the disclosure of which is hereby incorporated by reference. These multi-limbed fibers are described as comprising a solid filament of regenerated cellulosic material having a decitex of less than 5.0 and a multi-limbed cross-section, each limb having a length-to-width ratio of at least 2:1. The fibers are preferably staple length fibers having three or four limbs and a generally symmetrical cross-sectional shape, e.g., Y-, X, H, or T-shaped. A preferred cross-sectional shape is Y-shaped having an angle between limbs of about 120°. Preferred regenerated cellulosic material are viscose having a cellulose content of 5 to 12 wt-% and a caustic soda content of 4 to 10 wt-%. The fibers are preferably spun having a salt figure of 4.0 to 12.0. It is expected that any multi-limbed commercial fiber or even other such fibers, not currently commercially available, would be useful in the practice of the present invention. It is merely required that the fibers lead to an absorbent body having a relatively high specific absorption capacity which is increased by the addition of a less absorbent, non-limbed fiber to form a fibrous absorbent body.

The specific absorption capacity of a fibrous absorbent body including the multi-limbed, regenerated cellulosic fibers described above is increased by adding an amount of non-limbed cellulosic fibers. A representative, non-limiting list of cellulosic fibers includes natural fibers such as cotton, wood pulp, jute, bagasse, silk, wool, and the like; and processed fibers such as regenerated cellulose, cellulose acetate, cellulose nitrate, rayon, and the like. Preferably, the non-limbed cellulosic fibers are rayon or cotton, and more preferably, the fibers are rayon.

These non-limbed fibers are less absorbent, i.e., have a lower specific absorption capacity, than the multi-limbed, regenerated cellulosic fibers. However, adding an effective, specific absorption capacity-improving amount of non-limbed cellulosic fibers to the multi-limbed fibers surprisingly increases the specific absorption capacity of the resulting absorbent body. This increase is preferably to at least about 102% of the specific absorption capacity of a similar absorbent body made of the multi-limbed fibers alone. More preferably, the specific absorption capacity increases to at least about 105%.

We have found that adding an amount up to about 60 wt-% of the non-limbed cellulosic fibers can improve the specific absorption capacity of an absorbent body having the multi-limbed cellulosic fibers. Preferably, the non-limbed fibers are present at about 5 to about 50 wt-% of the absorbent body, and more preferably, at about 10 to about 30 wt-% of the absorbent body. Thus, preferred mixtures of fibers include about 1 to about 60 wt-% non-limbed fibers and about 99 to about 40 wt-% multi-limbed fibers; more preferred mixtures include about 5 to about 50 wt-% non-limbed fibers and about 95 to about 50 wt-% multi-limbed fibers; and most preferred mixtures include about 10 to about 30 wt-% non-limbed fibers and about 90 to about 70 wt-% multi-limbed fibers.

Additional fibers may also be included in the absorbent body. These additional fibers may include synthetic fibers such as polyesters, polyvinyl alcohols, polyolefins, polyamines, polyamides, polyacrylonitriles, and the like. These fibers may be included to add desirable characteristics to the absorbent body. For example, hydrophobic fibers may be used in outer surfaces of the body to reduce surface wetness and hydrophilic fibers may be used to increase the rate of fluid transport into and throughout the body.

The non-limbed and multi-limbed fibers are preferably blended to a substantially uniform mixture of fibers. These fiber blending operations are known to those of ordinary skill in the art. For example, the fibers can be continuously metered into a saw-tooth opener. The blended fibers can be transported, e.g., by air through a conduit to a carding station to form a fibrous web. The fibrous web is preferably calendered to impart a minor amount of compression. This web can be further processed to form an absorbent body. For example, the web can be used to form an absorbent layer in a sanitary napkin, a diaper, or an adult incontinence device. In addition, the web can be formed into a tampon. In a tampon forming process, the web can be formed into a narrow, fibrous sliver and spirally wound to form a tampon blank. In addition, a liquid-permeable cover material can be wrapped around the tampon blank to substantially contain the fibrous absorbent portion of the tampon.

This tampon blank can then be pressed into a tampon. Such tampon blank compression is known to those of ordinary skill in the art. For example, the tampon can be formed according to Messing et al., U.S. Pat. No. 3,422,496, or the commonly assigned, applications, Friese et al., U.S. Ser. No. 07/596,454, now abandoned, and Schoelling, U.S. Ser. No. 08/196,664, now abandoned each of which is herein incorporated by reference.

EXAMPLES

The improved absorbent characteristics of the present invention can be further illustrated according to the following examples.

Example 1

A series of fibrous webs were formed by adding a measured amount of multi-limbed regenerated cellulosic staple fibers (Galaxy® rayon fibers, 3.3 denier, having a fiber length of about 30 mm, available from Courtaulds Fibres, London, England) and non-limbed regenerated cellulosic staple fibers (Danufil® rayon fibers, 3.6 denier, having a fiber length of about 30 mm, available from Hoechst Kehlheim, Kehlheim, Germany) having the compositions identified in Table 1 below. For each web, the fibers were intimately mixed in and carded to form the fibrous web. This web was then calendered.

TABLE 1

| Test Product | Sample Size (n) | Avg. Wt. (g) | Wt-% Galaxy (%) | Wt. % Rayon (%) |
|---|---|---|---|---|
| Comp. Ex. A | 5 | 2.5 | 100 | 0 |
| Comp. Ex. B | 5 | 2.5 | 0 | 100 |
| Ex. C | 5 | 2.5 | 75 | 25 |
| Ex. D | 5 | 2.5 | 50 | 50 |
| Ex. E | 5 | 2.5 | 25 | 75 |

The specific absorption capacity of these webs were then measured according to the following procedure:

The fibrous web was cut to provide a fibrous sample strip with a weight of 2.5 g. The sample strip was then saturated with water and left to drain the excess water for a period of five minutes. The sample strip was then weighed, and the amount of absorbed water was calculated. The results of these measurements are displayed below in Table 2.

TABLE 2

| Test Product | Absorpt. (g) | Std. Dev. (g) | Specific Absorpt. (g/g) |
|---|---|---|---|
| Comp. Ex. A | 33.69 | 0.35 | 13.48 |
| Comp. Ex. B | 29.24 | 0.73 | 11.69 |
| Ex. C | 33.99 | 0.55 | 13.60 |
| Ex. D | 32.31 | 0.77 | 12.92 |
| Ex. E | 29.43 | 0.53 | 11.77 |

These data are also plotted in FIG. 1. It can be seen that an absorbent web of 100% multi-limbed rayon fiber has an absorption capacity which is greater than that of an absorbent web of 100% non-limbed rayon fiber. Unexpectedly, a blend of multi-limbed and up to about 30 wt-% non-limbed rayon fiber appears to increase the specific absorption above that of an absorbent body of 100 wt-% of the more absorbent multi-limbed fibers. Thus, these data illustrate that the incorporation of non-limbed rayon fibers to the multi-limbed rayon fibers provides a synergistic increase in the specific absorption capacity of absorbent webs.

Example 2

A second series of fibrous webs was formed according to the following procedure: The fiber components were weighed using a component scale, mixed together in a bale breaker and subsequently opened in a saw-tooth opener. The resulting blend was carded to obtain the fibrous web. The composition of these webs is identified below in Table 3. The multi-limbed and non-limbed fibers used in this Example 2 were the same as used in Example 1 above. The cotton used in this example was Cotton combers, supplied by Edward Hall, Stockport, England, having a fiber length of about 9 mm to 13 mm.

TABLE 3

| Test Product | Sample Size (n) | Avg. Wt. (g) | Wt-% Galaxy (%) | Wt.-% Rayon (%) | Wt-% Cotton (%) |
|---|---|---|---|---|---|
| Comp. Ex. F | 25 | 2.6 | 100 | 0 | 0 |
| Comp. Ex. G | 25 | 2.6 | 0 | 100 | 0 |
| Ex. H | 25 | 2.6 | 75 | 25 | 0 |
| Ex. I | 25 | 2.6 | 50 | 50 | 0 |
| Ex. J | 25 | 2.6 | 25 | 75 | 0 |
| Ex. K | 25 | 2.6 | 75 | 0 | 25 |

These webs were then used to manufacture compressed, radially-expanding, generally cylindrical tampons according to the process of the commonly assigned, applications to Friese et al., U.S. Ser. No. 07/596,454, now abandoned and Schoelling, U.S. Ser. No. 08/196,664, now abandoned. These tampons were conditioned at 21° C., 65% relative humidity for at least 24 hours and pre-weighed. The conditioned tampons were then tested according to the procedure for U.S. Food and Drug Administration Syngina tests, using an aqueous test solution as modified by adding the test fluid rapidly until tampon saturation and performing the procedure at about 20° C. (room temperature). The results of these tests are illustrated below in Table 4.

TABLE 4

| Test Product | Syngina Absorpt. (g) | Std. Dev. (g) | Specific Syngina Absorp. (g/g) |
|---|---|---|---|
| Comp. Ex. F | 12.50 | 0.26 | 4.81 |
| Comp. Ex. G | 11.83 | 0.19 | 4.55 |
| Ex. H | 13.48 | 0.27 | 5.18 |
| Ex. I | 12.73 | 0.17 | 4.90 |
| Ex. J | 12.09 | 0.20 | 4.65 |
| Ex. K | 13.12 | 0.24 | 4.86 |

Figure 2:
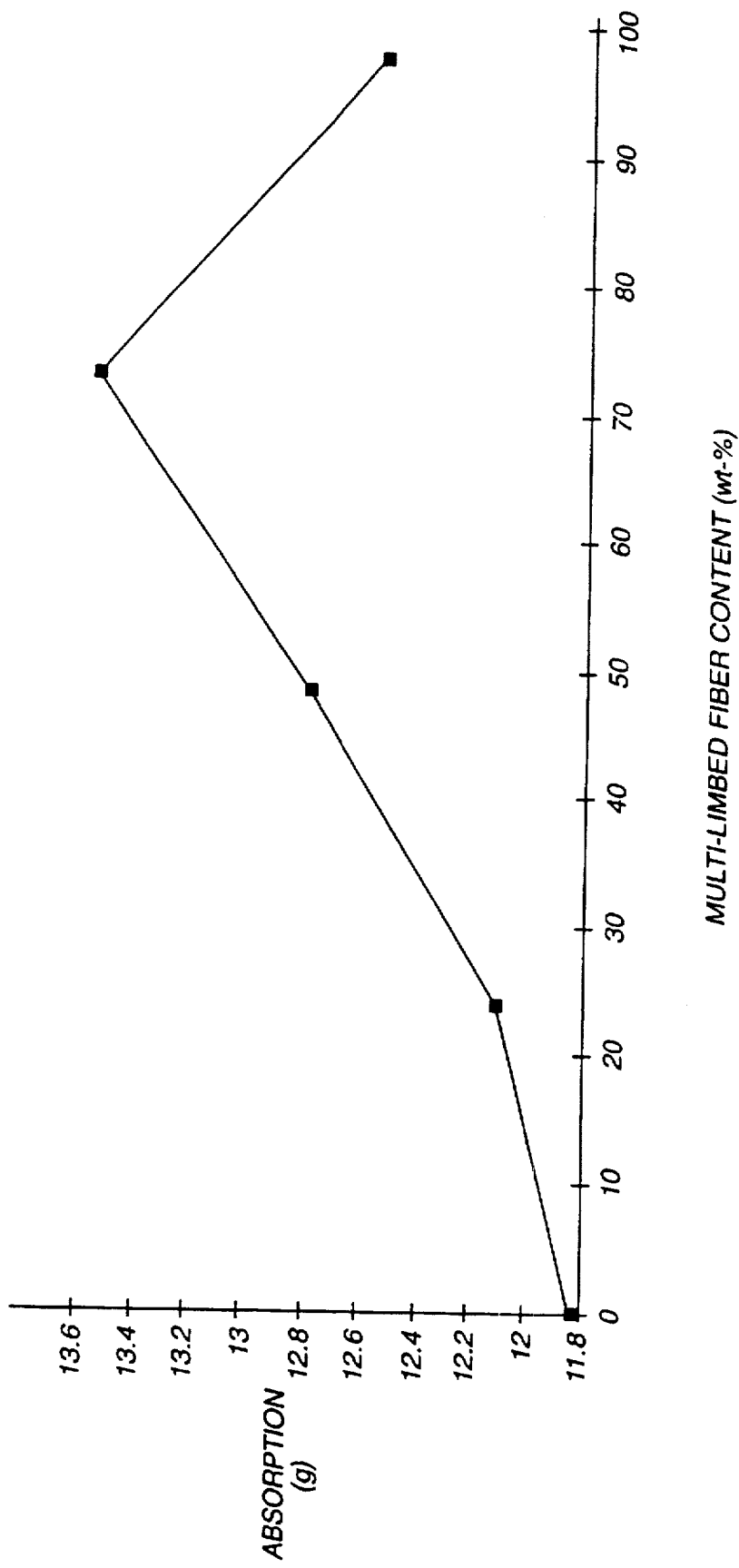
FIG. 2 illustrates a graphical representation of the data of Example 2.

Again, these data illustrate that the incorporation of non-limbed rayon fibers to the multi-limbed rayon fibers increases the specific absorption capacity of compressed absorbent tampons over that which would be expected by a mere addition of less absorbent fibers. These data are also plotted in FIG. 2. This effect can be seen up to about a 50 to 60 wt-% add-on of non-limbed rayon or cotton fibers.

The specification and examples above are presented to aid in the complete and non-limiting understanding of the invention disclosed herein. Since many variations and embodiments of the invention can be made without departing from its spirit and scope, the invention resides in the claims hereinafter appended.

What is claimed is:

1. An absorbent body having improved absorption capacity comprising a mixture of about 40 to about 99 wt-% of regenerated cellulosic fibers having a multi-limbed cross-section having at least three limbs and about 60 to about 1 wt-% of non-limbed, cellulosic fibers, the absorption capacity of said body being greater than that of a body formed of regenerated cellulosic fibers having multi-limbed cross-section not in admixture with non-limbed cellulosic fibers.

2. The absorbent body of claim 1 wherein said multi-limbed regenerated cellulosic fibers comprise viscose rayon staple fibers.

3. The absorbent body of claim 1 wherein said non-limbed cellulosic fibers comprise regenerated cellulosic fibers.

4. The absorbent body of claim 1 which comprises about 50 to about 95 wt-% of said multi-limbed fibers and about 50 to about 5 wt-% of said non-limbed fibers.

5. The absorbent body of claim 4 which comprises about 65 to about 85 wt-% of said multi-limbed fibers and about 35 to about 15 wt-% of said non-limbed fibers.

6. The absorbent body of claim 1 wherein said mixture of fibers is compressed.

7. An absorbent body having improved absorption capacity comprising a mixture of multi-limbed regenerated cellulosic fibers having at least three limbs and an effective amount of non-limbed, cellulosic fibers to increase the specific absorption capacity of the absorbent body beyond that of an absorbent body composed of multi-limbed regenerated cellulosic fibers not in admixture with non-limbed cellulosic fibers.

8. The absorbent body of claim 7 which comprises an effective amount of said non-limbed fibers to increase the specific absorption capacity to at least about 105% of the specific absorption capacity of a similar absorbent body of 100 wt-% multi-limbed fibers.

9. A method of increasing the absorption capacity of an absorbent body having multi-limbed regenerated cellulosic staple fibers comprising the steps of:

combining an effective amount of non-limbed cellulosic staple fibers to increase the absorption capacity of the absorbent body with said multi-limbed regenerated cellulosic staple fibers, wherein said multi-limbed fibers have at least three limbs; and forming a web comprising a substantially intimate mixture of said combination of fibers, the absorption capacity of said body being greater than that of a body formed of regenerated cellulosic fibers having multi-limbed cross-section not in admixture with non-limbed cellulosic fibers.

10. The method of claim 9 further comprising compressing the web.

11. A method of forming a tampon comprising the steps of:

combining about 1 to about 60 wt-% of non-limbed cellulosic staple fibers with about 99 to about 40 wt-% of multi-limbed regenerated cellulosic staple fibers, wherein said multi-limbed fibers have at least three limbs;

forming said fibers into a tampon blank, the absorption capacity of said blank being greater than that of a blank formed of multi-limbed regenerated cellulosic fibers not in admixture with non-limbed cellulosic fibers;

compressing said tampon blank to form said tampon.

12. The method of claim 11 which further comprises covering said tampon blank with a cover material.

13. The method of claim 11 wherein the step of compressing the tampon blank comprises a fibrous core substantially surrounding the central axis, the core having a first average density, and a plurality of ribs which extend radially from the core, wherein each rib is separated from adjacent ribs where it is attached to the core and each rib contacts adjacent ribs proximate the circumferential surface of the tampon.

14. The absorbent body of claim 1 wherein said non-limbed cellulosic fibers comprise cotton fibers.

* * * * *